United States Patent [19]
Abele et al.

[11] Patent Number: 5,403,311
[45] Date of Patent: Apr. 4, 1995

[54] ELECTRO-COAGULATION AND ABLATION AND OTHER ELECTROTHERAPEUTIC TREATMENTS OF BODY TISSUE

[75] Inventors: John E. Abele, Concord; Steven Rowe, Belmont; Christopher A. Rowland, Marlboro, all of Mass.; Michael G. Vergano, Cumberland, R.I.

[73] Assignee: Boston Scientific Corporation, Watertown, Mass.

[21] Appl. No.: 38,903

[22] Filed: Mar. 29, 1993

[51] Int. Cl.⁶ .............................................. A61B 17/39
[52] U.S. Cl. ........................................ 606/49; 606/50; 606/45; 606/48; 604/21
[58] Field of Search .................... 604/20–22; 606/37–41, 45–50; 607/104, 105, 120, 122, 125, 126

[56] References Cited

U.S. PATENT DOCUMENTS

| | | |
|---|---|---|
| 1,814,791 | 7/1931 | Ende . |
| 3,634,652 | 1/1972 | Shimizu et al. . |
| 3,920,021 | 11/1975 | Hiltebrandt . |
| 4,016,881 | 4/1977 | Rioux et al. . |
| 4,071,028 | 1/1978 | Perkins . |
| 4,196,734 | 4/1980 | Harris . |
| 4,228,800 | 10/1980 | Degler, Jr. et al. . |
| 4,248,231 | 2/1981 | Herczog et al. . |
| 4,269,174 | 5/1981 | Adair .......................... 606/49 |
| 4,313,431 | 2/1982 | Frank .......................... 606/16 |
| 4,449,528 | 5/1984 | Auth et al. . |
| 4,476,862 | 10/1984 | Pao . |
| 4,532,924 | 8/1985 | Auth et al. . |
| 4,543,090 | 9/1985 | McCoy . |
| 4,582,057 | 4/1986 | Auth et al. . |
| 4,637,392 | 1/1987 | Sorochenko . |
| 4,641,649 | 2/1987 | Walinsky et al. . |
| 4,660,571 | 4/1987 | Hess et al. ........................... 606/41 |
| 4,674,499 | 6/1987 | Pao . |
| 4,685,459 | 8/1987 | Koch et al. . |
| 4,706,667 | 11/1987 | Roos . |
| 4,805,616 | 2/1989 | Pao . |
| 4,953,559 | 9/1990 | Salerno . |
| 4,955,377 | 9/1990 | Lennox et al. . |
| 4,998,933 | 3/1991 | Egers et al. ........................ 606/44 |
| 5,007,908 | 4/1991 | Rydell ................................ 606/50 |
| 5,078,717 | 1/1992 | Parins et al. ........................ 606/48 |
| 5,085,652 | 2/1992 | Rydell ................................ 606/50 |
| 5,106,386 | 4/1992 | Isner et al. ......................... 606/15 |
| 5,109,830 | 5/1992 | Cho ..................................... 606/7 |
| 5,122,137 | 6/1992 | Lennox ............................... 606/40 |
| 5,125,928 | 6/1992 | Parins et al. ........................ 606/48 |
| 5,281,218 | 1/1994 | Imran . |

OTHER PUBLICATIONS

R. L. Protell et al., "Computer-Assisted Electrocoagulation: Bipolar vs. Monopolar in the Treatment of Experimental Gastric Ulcer Bleeding".

Bard Interventional Products, "Bard ® Bipolar Hemostasis Probe".

(List continued on next page.)

*Primary Examiner*—Stephen C. Pellegrino
*Assistant Examiner*—Michael Peffley
*Attorney, Agent, or Firm*—Fish & Richardson

[57] ABSTRACT

A catheter includes a flexible elongated catheter body that defines a needle-receiving, or probe-receiving, lumen, a retractable tissue-penetrable needle, or probe, and an electrode mounted on the distal portion of the catheter body. The needle provides a fluid passage for introducing fluid into tissue to permit the introduction of sclerotic agents for enhancing electrocoagulation of the tissue, heat-responsive drugs for improving the bonding to tissue surfaces, or vaso-constrictor drugs. The probe can also have a passage for fluid. The electrode can provide bipolar electro-coagulation of tissue in combination with an additional electrode mounted on the catheter body, or alternatively, the electrode can be employed in combination with either the needle or probe to establish a bipolar electro-coagulation path through tissue. The needle, or probe, in combination with an external electrode can be used to provide unipolar electro-coagulation, or ablation. In certain instances, the electrode can be used to provide a mapping function inside cardiac chambers.

19 Claims, 4 Drawing Sheets

OTHER PUBLICATIONS

Microvasive ® Gold Probe ™ —The Next Generation in Bipolar Hemostasis.

Microvasive ® Boston Scienfific Corporation, "Variject ™ Sclerotherapy Needles", 1991.

Microvasive ® Boston Scientific Corporation, "Hemoject ™ Injection Therapy Needles", 1991.

J. P. Moore et al., "Evaluation of Bipolar Electrocoagulation in Canine Stomachs", vol. 24, No. 4, 1978, pp. 148–151.

Robert L. Protell et al., "The Heater Probe: A New Endoscopic Method for Stopping Massive Gastrointestinal Bleeding", vol. 74, No. 2, 1978, pp. 257–262.

OES Evolution, "OES Upper Gastrointestinal Fiberscope Olympus GIF Type XQ20".

Biosearch ® Medical Products, Inc., "Dobbhoff ® Bipolar Coagulation Probe".

Wilson–Cook Medical, Inc., "Varices Injectors", pp. 43–44.

David A. Gilbert et al., "Nonsurgical Management of Acute Nonvariceal Upper Gastrointestinal Bleeding", pp. 349–395.

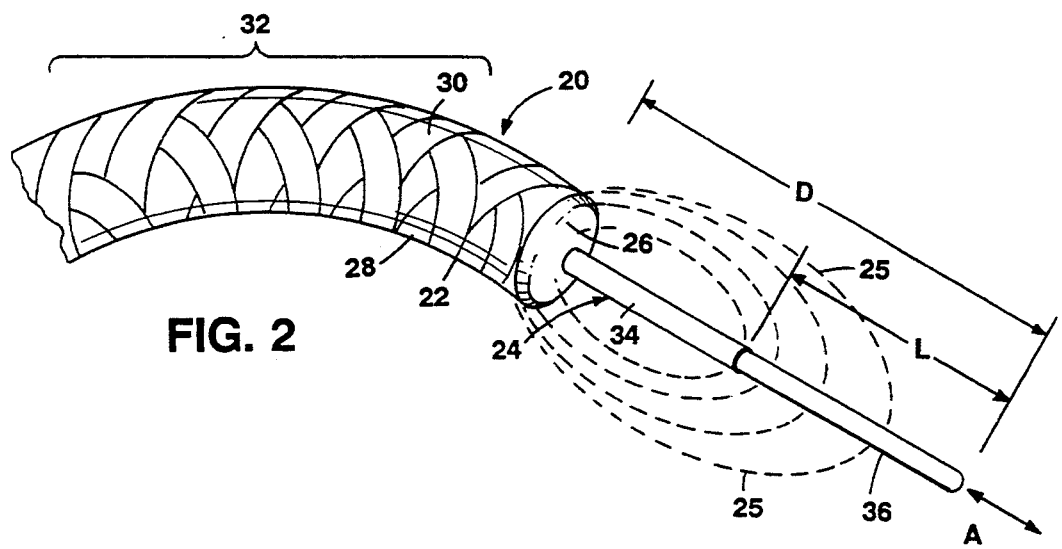
FIG. 2
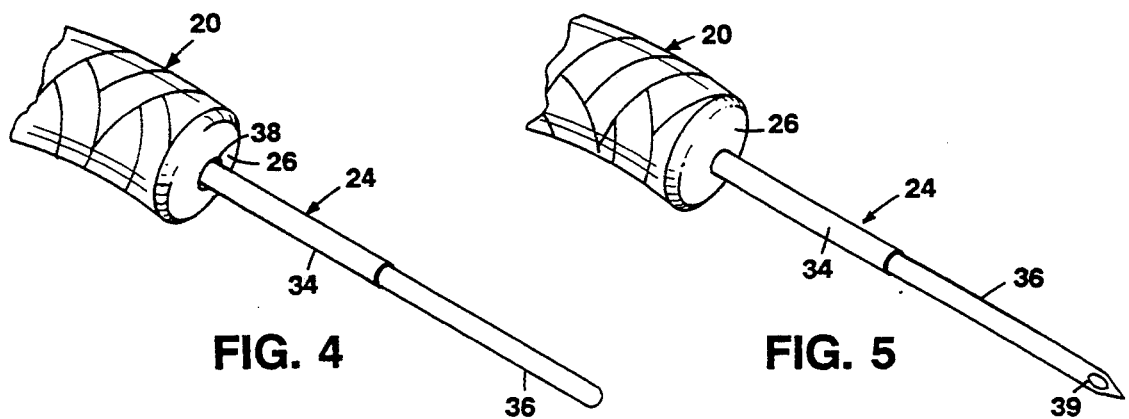
FIG. 4
FIG. 5

ELECTRO-COAGULATION AND ABLATION AND OTHER ELECTROTHERAPEUTIC TREATMENTS OF BODY TISSUE

BACKGROUND OF THE INVENTION

The invention relates to electro-coagulation of tissue of the body and to the performance of other modes of electrotherapy, especially within the body, via catheters.

As is known by those of skill in the art, radiofrequency energy of suitable current density and wave form to perform electro-coagulation (cauterization) may be used to seal potential hemorrhaging or bleeding areas by electro-coagulation of tissue and blood, without cutting. With this technique RF coagulation current applied to the tissue generates heat by resistive losses in the conductive tissue. The resulting heat drives out extracellular and intracellular water resulting in coagulation necrosis. Similarly, the technique is used to cause necrosis of (i.e. "ablate") tissue that is performing improperly, especially arrhythmic heart tissue.

One method of performing electrocoagulation of tissue is through the use of mono-polar electrodes, in which one electrode is carried by a catheter to the site while the other electrode is an exterior ground plate placed on the skin of the patient. In another method, a bipolar catheter is employed. An example is the Gold Probe TM, manufactured by Boston Scientific Corporation, the assignee of the present invention. It comprises a flexible catheter with a distal tip formed of a ceramic cylinder having a hemispherical end. The ceramic tip includes a pair of gold spiral electrodes applied to its cylindrical surface and domed end. The spiral electrodes are separated by insulated areas in an arrangement resembling the stripes of a barber pole. RF current flowing between the electrodes heats and cauterizes the tissue which is contacted by the tip of the catheter. The catheter is constructed to be employed through the working channel of an endoscope to seal potential bleeding sites such as in the GI tract or the esophagus.

In another instance, RF coagulation catheters of other forms have been introduced through the vascular system to the heart to remedy arrhythmia. In this case electrophysiological evaluation is performed at locations on the heart, and when a site requiring treatment is found, the catheter is used to ablate or deaden the tissue to correct the arrhythmia.

Other forms of treatment to address bleeding sites or sites requiring ablation have included the use of catheter-placed needles that inject drug agents such as vasoconstrictors for reducing bleeding and absolute ethanol for ablation of tissue.

In these and similar instances of therapy the prior art has overlooked possibilities of improving the location, depth, degree and accuracy of control of the treatment and the possibilities of multi-modality treatment employing a single catheter.

SUMMARY OF THE INVENTION

In one aspect, the invention features a catheter for passage into a living body to perform therapy, including a flexible pushable elongated catheter member and a distal tissue-penetrable rf current electro-coagulation probe selectively projectable from and retractable into the distal end of the catheter member by actuation motion applied to a proximal region of the catheter. The probe is sized to penetrate tissue against which it is pressed.

Embodiments of the invention include one or more important further features as follows. The projectable and retractable distal electro-coagulation probe forms a first electro-coagulation electrode for electrical contact with tissue beneath the surface, and the distal end of the catheter member includes a second electro-coagulation electrode for contact with the surface of the tissue, the electrodes being cooperatively related to provide a bipolar electro-coagulation path through the tissue. After the probe penetrates the tissue, the catheter and probe are cooperatively constructed to enable manipulation of the catheter to effectively temporarily anchor the probe within the tissue.

Thus, a projectable and retractable probe with the ability to precisely control the extent of tissue penetration provides the physician with the ability to electrocoagulate tissue at increased penetration depths (e.g., to about 6 mm) with substantially greater control. Upon determining a tissue site requiring electrocoagulation ablation, the probe forming the first electrode is injected into the tissue, the second electrode moved into contact with the tissue surface and the probe depth precisely adjusted by the physician at the proximal end of the catheter. RF current from an external RF current source applied to the electrodes provides a coagulation area with a larger surface greater uniformity.

In a particular aspect of the invention, a catheter and a method for its use is provided for ablation of cardiac tissue by repeatedly contacting the tissue of a beating heart at different locations with mapping electrodes in mapping steps, so that the electrical condition at selected locations can be sensed. When a location is determined on the heart where the sensed condition indicates a problem requiring ablation, and thereafter, in an ablation step, the heart tissue is ablated in that location. The catheter includes a mapping/electro-coagulation catheter which includes an elongated catheter member capable of being introduced through the vasculature or a guiding catheter to access the heart, and a distal tissue-penetrable probe selectively projectable from and retractable into the distal end of the catheter member. The probe is sized to penetrate the heart tissue and the catheter is constructed for further manipulation to temporarily anchor the probe within the heart tissue to enable the catheter, while the same position is assured, to perform a mapping step and a subsequent ablation step.

Embodiments of the invention include the following features. The projectable and retractable distal probe forms a first electro-coagulation electrode for electrical contact with tissue beneath the surface, and the distal end of the catheter member includes a second electro-coagulation electrode for electrical contact with the surface of tissue, the electrodes being cooperatively related to provide a bipolar electro-coagulation path through the tissue. The probe is constructed to serve as a mapping electrode.

As a result, the retractable probe of the catheter acts as an anchor to provide greater positional stability of the probe for various probe positions and angles during the mapping and ablation procedure. The position of the probe can be controlled by the physician at the proximal end of the catheter with greater confidence. Control of the extent of projection provides deeper and more precise electrocoagulation during the ablation procedure. The catheter may include multiple spaced apart tissue-penetrable probes each projectable from the catheter member.

In another aspect of the invention, a bipolar electro-coagulation catheter includes an elongated catheter member and a relatively axially movable electro-coagulation probe electrode mounted for projection from and retraction into the distal end of the catheter member and sized to penetrate tissue. The catheter member is precurved, capable of being torqued to adjust its position in the body and carries at least a second electro-coagulation electrode in the vicinity of the projectable and retractable probe. The electrode may be a ring-form electrode surrounding and insulated from the retractable probe. Alternatively, the catheter member may include a set of spaced electrodes disposed at a distal end which are electrically connected together in a first mode of operation and in a second mode of operation are configured to perform bipolar coagulation or mapping of the surface tissue without participation of the probe. The precurve provided to the catheter member enables the physician through twisting of the catheter to accurately guide and project the probe into the tissue (generally under endoscopic visualization) at the desired injection site.

In another aspect of the invention, a bipolar coagulation catheter has a dome form at a distal end with a conductive coating on the dome to form a tissue-engageable electrode of one polarity and a projectable and retractable electrically conductive hollow needle projectable axially from the end of the dome providing an electrode of opposite polarity. The electrodes are insulated from each other and are capable of providing bipolar coagulation. The hollow needle is capable of introducing a fluid, (e.g., a vasoconstrictor, sclerotic, topical anesthetic, or heat responsive drug) into the tissue to enable a further modality of use. Introducing a vasoconstrictive or sclerotic agent through the hollow needle reduces the tissue area that has to be coagulated enabling the treatment of larger and more serious bleed sites. When a heat responsive drug is introduced, coagulation current applied to the probe provides the source of heat. Thus, in general, an electrocoagulation catheter having the added capability of providing pharmaceutical agents to enhance the electrocoagulation action is provided. With this capability a physician can respond to the specific nature of a problem and can apply in succession several modalities while observing the response at each stage. The catheter may include a pair of said probes each including an electro-coagulation electrode, such that the two probes when projected into tissue and adapted for connection to opposite poles of an rf source produce subsurface bipolar coagulation.

In another aspect of the invention, a coagulation instrument and a method for its use includes a first electrode in the form of a tissue-penetrable, projectable and retractable probe mounted on a support, a second electrode contacting the patient and a wiping member having an end closely surrounding the probe. On retraction of the probe, substance that is adhered to the sides of the probe is wiped off by the end of the wiping member and the exposed electrode surface of the first probe is sized to produce coagulation current density sufficient to heat the surrounding tissue and the sides of the probe to tissue-adhering level. The probe is adapted to be inserted into tissue while the second electrode contacts the patient, whereby, upon applying rf coagulation current between the electrodes sufficient to produce coagulation, adherence of the coagulated tissue and blood substance to the sides of the probe occurs. Thereafter, while holding the instrument against the tissue, the probe is retracted causing adhered coagulated substance to be wiped therefrom by the end of the wiping member and deposited in a compressed mass at the point of entry into the tissue, to provide an autologous seal that is derived from the tissue.

Controlling the exposed electrode surface of the first probe allows the physician to control the coagulation current density of the first probe such that the degree of localized heating surrounding each electrode is controlled. In this way, the electrocoagulation procedure can be performed such that tissue surrounding the projectable first probe is heated to a higher temperature causing it to adhere to the probe. Upon retraction of the probe within the catheter, the coagulated tissue is wiped off the probe in a manner providing an autologous suture to seal the bleed at the point of injection.

Another aspect of the invention features a method of introducing a heat responsive drug in tissue including providing a bipolar coagulation instrument having a first electrode in the form of a tissue-penetratable and retractable probe, a second electrode surrounding the first electrode, the probe comprising a hollow needle, inserting the probe into tissue and contacting the second electrode with the surface of the tissue, introducing the drug into the tissue and applying rf coagulation current to the electrodes sufficient to heat the drug to an effective temperature by coagulation current.

Any one or all of the above aspects of the invention may include the following features. The catheter is sized and constructed for passage into a living body independently or may be introduced through the working channel of an endoscope or a guiding catheter. The electro-coagulation electrode of the catheter member is a conductive dome-form, tissue engageable member. The catheter member is of torqueable construction and has a precurved distal portion capable of being elastically deformed to conform to an introducing channel or lumen through which it passes into the body. The radiofrequency current applied to the probe has a level and waveform to produce electrocoagulation without cutting. The probe includes a wire adapted to be elastically deflected relative to the catheter member, after insertion of the wire into tissue, by lateral or rotational displacement of the catheter member to promote temporary anchoring of the probe within the tissue. The wire has a diameter of about 0.015 inch and is capable of projecting between 1 to 3.0 millimeters from the catheter for effective positioning. After the probe is advanced into the tissue, the proximal portion of the catheter is constructed to be translated or rotated relative to the probe to press the probe sideways against the tissue to apply side pressure to the probe to provide resistance to removal of the probe from the tissue. The probe is sized relative to a predetermined coagulation current setting to cause the probe to heat to the temperature range that causes coagulated tissue and blood substance to adhere to the sides of the probe during electro-coagulation, and the catheter includes means to wipe the adhered coagulated substance from the sides of the probe as the probe is retracted into the catheter member in a manner to deposit the wiped, coagulated substance at the coagulation site to form an autologous seal comprised of compressed coagulated substance. Adjustment of the length of axial extension of the probe is effective to determine the depth of penetration and thereby the depth of coagulation of tissue. The probe is sufficiently projectable to produce coagulation of 6 millimeters in depth in a uniform zone of coagulation. A thin electrically insulating sleeve surrounding and adjustable along the length of the probe is provided to controllably vary the length of the electrically conductive surface of the probe that is directly exposed to the tissue. The catheter is sized for passage via the working channel of an endoscope.

DESCRIPTION OF THE DRAWINGS

FIG. 2 is a perspective view of the distal end of the catheter of FIG. 1.

FIG. 4 is a perspective view of the distal end of an alternate embodiment of the catheter.

FIG. 5 is a perspective view of the distal end of an alternate embodiment of the catheter.

DESCRIPTION OF PREFERRED EMBODIMENTS

Figure 1:
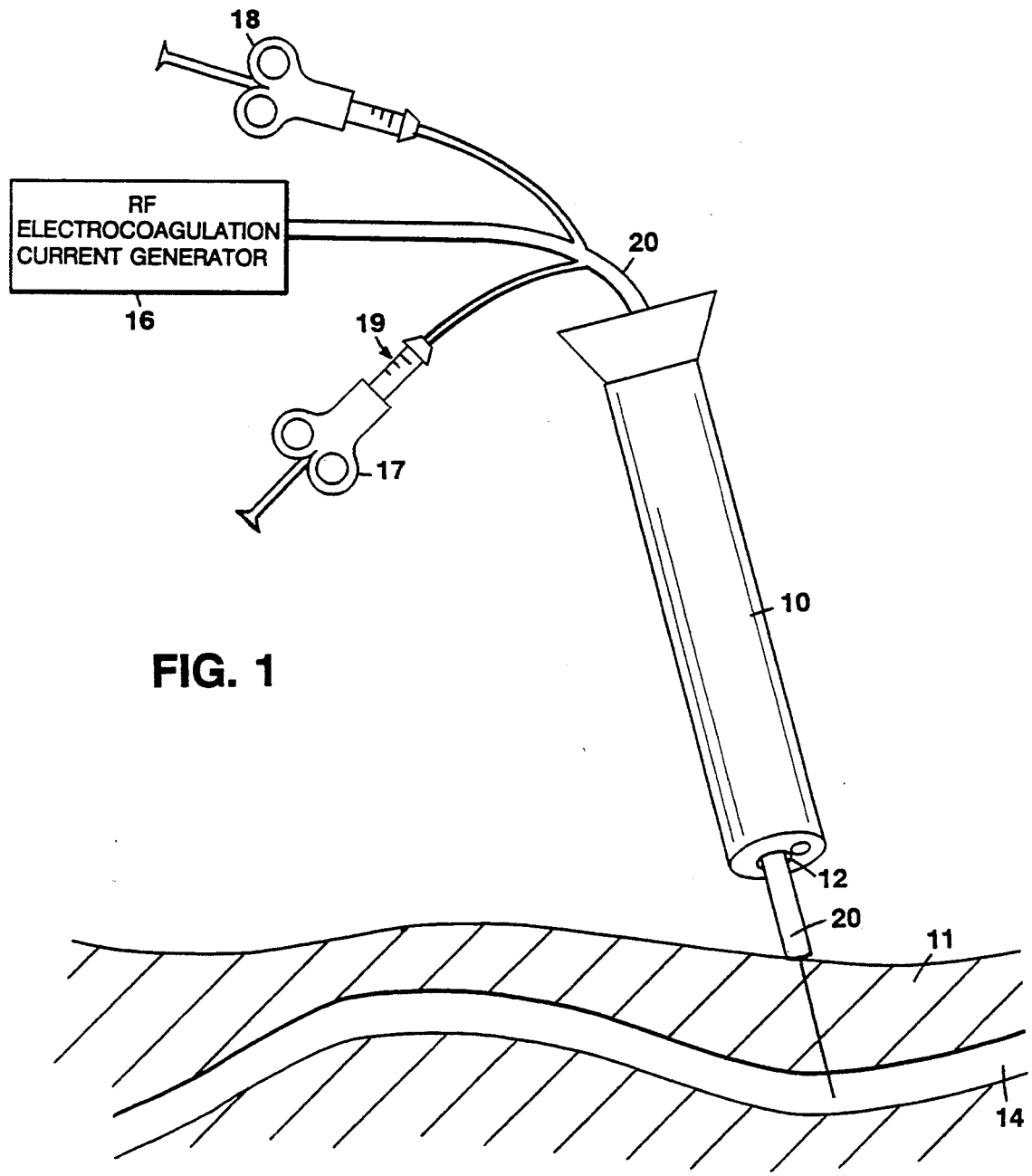
FIG. 1 is a diagrammatic view of a catheter of the invention disposed within an endoscope and provided to a blood vessel.

Referring to FIG. 1, a catheter 20, pushed through a working channel 12 of an endoscope 10, enters the human body 11 to a location a blood vessel 14 identified as a potential or actual bleeding site. The catheter 20 has an outer diameter sized to extend through the working channel 12 which has an inner diameter generally between 2.8 and 4 mm. The catheter includes a pair of electrodes that are connected to an RF electro-coagulation current generator 16 at a proximal end of the catheter.

As shown in FIG. 2, the distal end 22 of catheter 20 includes a catheter body 28, a probe 24, shown here to be coaxially disposed with catheter body 28 and an electrode ring assembly 26 on distal end 22 of catheter body 28. Ring electrode 26 is exposed for engagement with the surface of tissue. Probe 24 has an extremely small dimension, sized to penetrate tissue, and in one embodiment includes a hollow needle with a central sharp point and in another embodiment includes a fine wire with stiffness properties enabling tissue-penetration. The tissue-penetrable probe 24 is slidably supported within the catheter body 28 and can be adjusted axially in or out as indicated by arrow A by an actuating push-pull wire or cable that extends proximally to the proximal end through a lumen of the catheter body 28 to a handle 17 (FIG. 1). The catheter body 28 of this embodiment is constructed with a braided layer 30 that renders it torquable by the physician, to orient the catheter tip to a desired orientation. Braided layer 30 is fabricated from cross braided stainless steel filaments having diameters of about 0.003 inches for providing, as a mesh, the necessary outer conductor extending from electrode ring 26 to an RF electro-coagulation current generator 16. Activation of RF current generator 16 provides an RF current flow between probe 24 and electrode ring 26 as indicated by current lines 25. Catheter body 28 is also included of suitable resinous thermoplastic layers that enables the distal portion of the catheter body to be precurved, at 32, in the course of manufacture. Precurve 32 is thermoformed such that is straightened as it passes through endoscope 10 but upon exiting working channel 12 springs back to its precurved shape. The shape of precurve 32 provides the physician with greater control in guiding catheter 20 to a desired position.

The coaxial probe 24 includes, a thin insulating sheath 34 surrounding an electrically conductive needle tip 36. Coaxial probe 24 is projectable and retractable from catheter body 28 via a pull wire extending through a lumen of catheter body 28 and connected to handle 17 so that its extended length can be controlled by the physician. In its fully projected condition catheter probe 24 extends a distance D of about 6 mm from catheter body 28. The uninsulated portion of the coaxial probe 24 is a needle tip 36 having an outer diameter between 0.015 and 0.020 inches and extends from the insulating sheath 34 a distance between 1.0–3.0 mm. Needle tip 36 represents the electrically conductive portion of the electrode. The insulating sheath 34, fabricated e.g. from polyamide, has an outer diameter of 0.024 inches and an inner diameter corresponding to the outer diameter of coaxial probe 24 to provide electrical isolation between the probe 24 and electrode ring 26. Sheath 34 may be fixed. In a preferred embodiment, however, it is provided as an independently projectable and retractable sleeve into which needle tip 36 is fitted with a sliding fit. As was the case with catheter probe 24, needle tip 36 is also connected through a pull wire to handle 18 so that the length L of the needle tip 36 extending from insulating sheath 34 is controlled. Thus, the physician can independently control the depth of insertion of coaxial probe 24 within the tissue as well as the degree of exposed conductive surface of needle tip 36.

In the embodiment of FIGS. 1 and 2, the outer ring electrode 26 has approximately the same effective electrically conductive area as the needle tip 36 so that the current density at the two electrodes is approximately equal. In other preferred embodiments, the probe area and other parameters are selected so that the current density at the probe is larger for special reasons described below.

For good coagulation, the coaxial probe 24 is injected to penetrate the tissue site where coagulation is to be achieved and by slidable adjustment between the two parts, actuated by the physician using handle 17 from the proximal end, the electrode ring 26 is moved relatively forward until the appropriate depth separation between probe tip and catheter body tip is obtained, with electrode ring 26 engaged upon the surface of the tissue. Thereafter an RF electro-coagulation current generating source, such as an Endostat® generator manufactured by Medical Scientific, Inc., Foxboro, Mass., connected between the electrodes, is energized to cause rf coagulation current to flow, to thereby electro-coagulate the tissue.

The general principle employed by the instrument is that coagulation without cutting can be accomplished by the application of RF current of the proper wave form and energy, that will coagulate tissue and blood, as is well known to the art.

With a prototype of this design using the Endostat ® power supply and liver as test tissue, it has been shown that a depth of coagulation as much as 6mm can be achieved while producing uniform coagulation, a coagulation zone substantially larger than possible with certain prior instruments. By selectively retracting and projecting the conductive probe into and out of the outer catheter body, the depth of coagulation is accurately controlled.

It is desirable, particularly when seeking to coagulate a blood vessel that is beneath the tissue surface, to employ the depth-controlled endoscopic bipolar catheter of the present invention.

The provision of precurve 32 to the catheter body 28, and the torquability provided by the braid 30 enables the physician by twisting and pushing under endoscopic visualization, to finely guide the catheter 20 to the site for coagulation while holding the endoscope 10 steady as a reference platform. Upon achieving proper placement, the physician projects the probe into the tissue to a well-controlled amount which can be determined by the physician by observing markings 19 (FIG. 1) on the proximal end of the push-pull actuation wire. According to the invention, the projectable probe in the form of a needle or wire as an extendable electrode probe, is thus projected into the tissue or blood vessel, and rf coagulation current is applied in a bi-polar fashion between the small conductive probe 24 and the electrode ring 26 on the distal end 22 of the catheter 20.

By use of these features, improvement is obtained in the fine control of location and depth of coagulation.

When also employing the axially adjustable insulation sleeve 34, mentioned above, it becomes possible to adjust the surface area of the probe as may be indicated. For instance if adherence or sticking of coagulated blood and tissue to the probe appears to be a problem, the sleeve may be withdrawn to increase the exposed surface area of the conductive probe and reduce current density.

As is known, the relative area of the two electrodes determines which electrode heats to the higher temperature for a given current density. The smaller area electrode has the greater current density and can reach a higher temperature. It is important to note that heating of the electrodes is passively provided by the I²R heating of the tissue surrounding the electrodes.

As is known in the art of electrosurgery, the electrode that heats the most may stick to the tissue depending upon the level of electro-coagulation current employed. This is referred to as "over heating". This sticking or adherence of coagulated substance is ordinarily viewed as a disadvantage because when the electrode is moved, the scab of coagulated tissue is disturbed and the bleeding may start again. This may be avoided by appropriate use of the independently adjustable insulation sleeve.

Figure 3A:
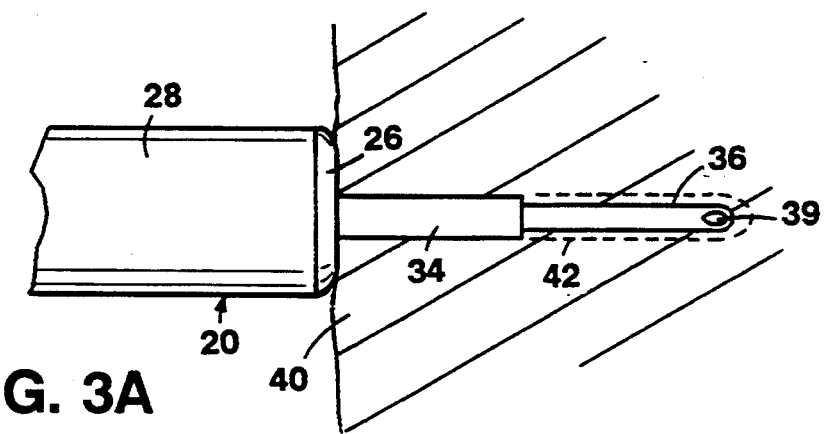
FIGS. 3A and 3B are a pair of side views demonstrating the electrocoagulation operation of the instrument.
Figure 3B:
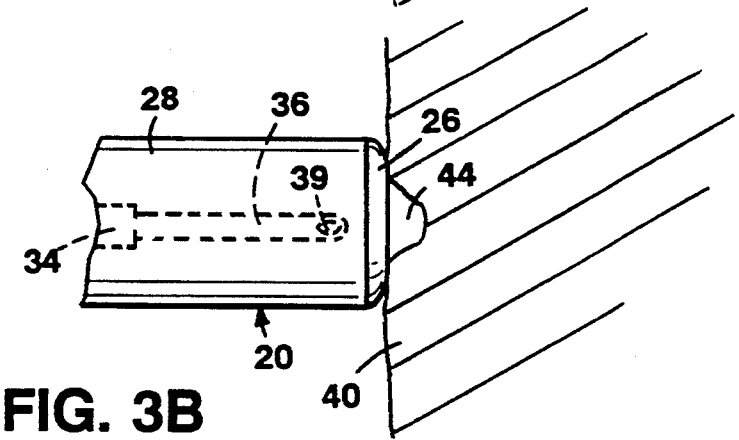

As diagrammatically shown in FIGS. 3A-3B, however, according to another aspect of the invention, advantage can be taken of this tissue-sticking phenomenon. As shown in FIG. 3A, after catheter 20 has been appropriately placed into position within a vessel wall 40, the exposed distal conductive needle tip 36 of the coaxial probe 24, is extended such that the effective conductive surface area of needle tip 36 is less than electrode ring 26, and at a preselected current level, is sized to heat to a higher range temperature, (i.e. "over heat"), so that the coagulated tissue or blood sticks to the exposed surface of the needle 36. The "sticking" effect caused by overheating of the needle tip 36 provides the additional advantage of providing a firmly secured or "anchored" needle tip 36 within the tissue. Referring now to FIG. 3B, after electrocoagulation, the small electrode probe 24 is pulled back into catheter body 28, causing the adhered coagulated substance 42 created by electrocoagulation to be "squeegeed" or wiped off of the needle tip 36 by the closely surrounding catheter body 28. By this action the necrotic or coagulated tissue, compressed by the wiping action is deposited in the tissue 42 that is next to the catheter electrode. This compressed coagulated substance forms effectively an autologous suture or seal 44 that fills in behind needle tip 36 and provides an improved repair that reduces the risk of further bleeding from the site.

The autologous "suture" or seal 44 produced by withdrawal of the overheated probe 24, where employed, is further modality that can enhance the capacity of the system to coagulate and stop the bleeding. This is especially useful in the case of large bleeders (large bleeding blood vessels).

In the examples so far noted, the projectable probe or needle 36 can be a fine conductive wire or it can be a hollow needle (FIG. 5).

Referring to FIG. 4, an irrigation passage 38 for providing perfusion fluid is disposed between the two electrodes 26, 36 to flush and cleanse the work site. Under some circumstances, even a clearance of a few thousandths of an inch is sufficient to inject a useful fluid, while returning a desirable squeegee effect for coagulated tissue. Alternatively, as shown in FIG. 5, an irrigation passage 39 may be provided through a hollow portion of needle 36.

The hollow needle 36 provides the capability of performing further multi-modalities therapy. For example passages 38, 39 may be used to introduce a vaso-constrictive agent or sclerotic to the coagulation site to constrict the local blood vessel and decrease blood flow to the area. After endoscopically guiding the catheter through the working channel to the site and projecting the needle into the tissue to a desired depth, the vasoconstrictor is injected into the bleeding blood vessel or tissue via the lumen of the needle. The resultant constriction reduces the area that has to be coagulated. Therefore, when electrocoagulation is subsequently performed by the instrument, better coagulation can be obtained, making it less likely for rebleeding to occur after coagulation.

In another example, a variety of chemicals for enhancing the electro-coagulation of the tissue, such as sclerotherapy agents may be introduced through passages 38, 39.

In still another example, agents which block the passage of electro-physiological impulses within tissue can be employed, which are particularly useful in correcting arrhythmia within a beating heart.

Figure 6:
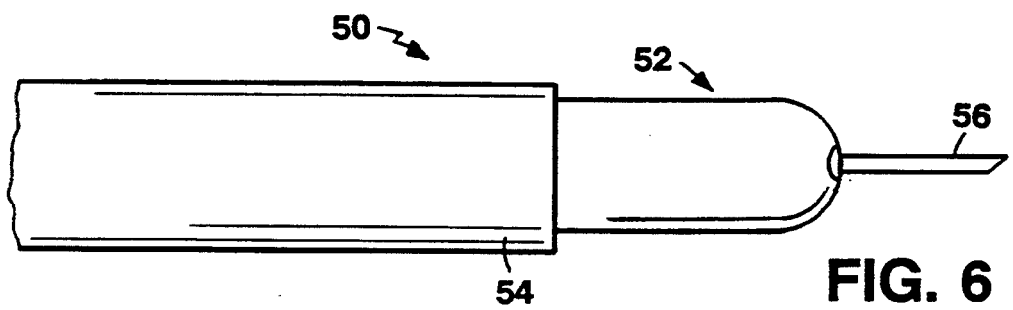
FIG. 6 is a side view of an alternate embodiment of the catheter with its probe projected.
Figure 7:
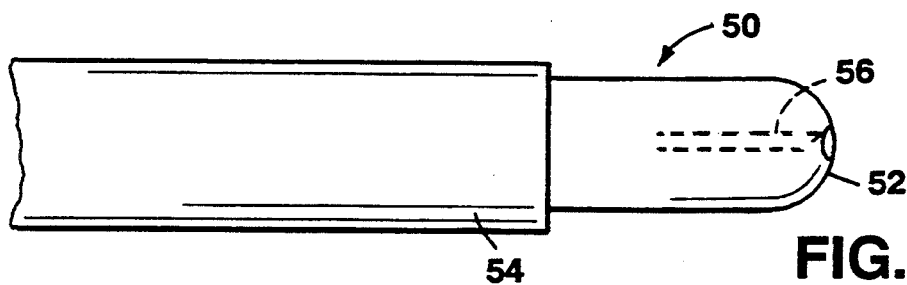
FIG. 7 is a side view of an alternate embodiment of the catheter with its probe retracted.

Referring now to FIG. 6, a distal end of a catheter 50 includes a rounded end portion 52 secured to the end of a catheter shaft 54. Rounded end portion 52 is fabricated from a refractory material such as ceramic and is entirely coated with a conductive metal, such as gold to provide a first electrode of the catheter. A projectable, tissue-penetrable needle tip electrode 56, representing a second electrode isolated from the gold coated first electrode, extends coaxially from end portion 52 which when coupled to a RF electrocoagulation current generator provides a bipolar coagulation catheter. As shown in FIG. 7, needle tip electrode 56 is retractable to permit the physician to better control the depth of coagulation in the manner described above in conjunction with FIG. 2.

Figure 8:
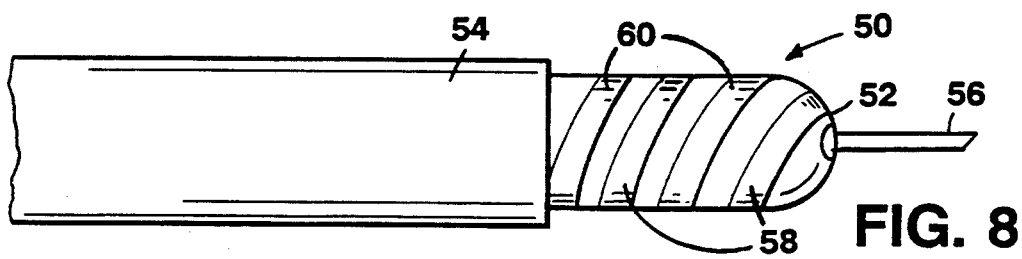
FIG. 8 is a side view of an alternate embodiment of the catheter.

As shown in FIG. 8, in another embodiment, rounded end portion 52 may include a pair of laser etched gold electrodes 58, 60 precisely spaced in a helical arrangement around end portion 52, in the manner employed by the Gold Probe TM, mentioned above. The projectable, tissue-penetrable needle tip electrode 56 extends coaxially from end portion 52 to provide a three-electrode (tri-polar) coagulation catheter. With the needle retracted, the instrument may be employed in the prior manner of the Gold Probe TM. When needed, the needle electrode may be extended and electrodes 58, 60 may be externally switched at the RF current generator 16 (FIG. 1) to form a single electrode, acting with needle tip electrode 56 to operate in bi-polar mode to produce deeper coagulation as described above. With this arrangement, the physician has added control over the coagulation depth or distribution of heat without removing the catheter to substitute a needle tip electrode having a different length or geometry.

It is appreciated that rounded end portion 52 may include irrigation ports for introducing cleansing fluids or sclerosing solutions as described above in conjunction with FIGS. 4 and 5.

Figure 9A:
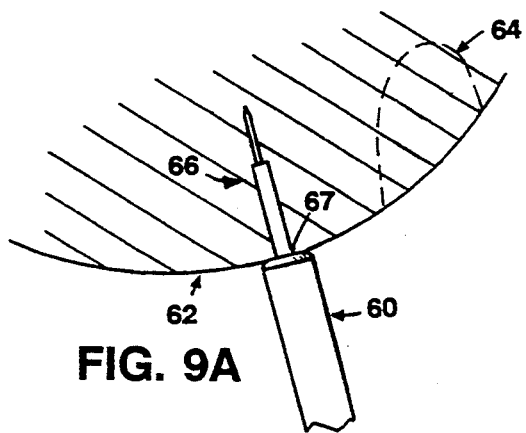
FIG. 9A and 9B are diagrammatic views demonstrating the operation of a mapping/electrocoagulation catheter.
Figure 9B:
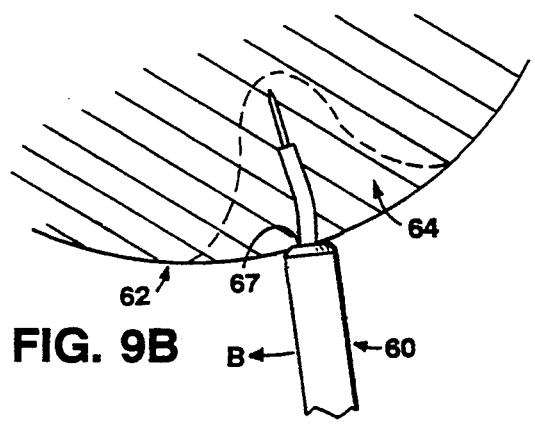

Referring to FIGS. 9A–9B, a process for providing cardiac ablation of arrhythmogenic tissue within the heart is shown. As is known by those in the art, arrhythmogenic tissue within the heart generally has faulty electrical conduction problems. Such electrical abnormality in the current flow of the heart causes problems of arrhythmia, generally the acceleration of the pulse of the heart. In one method of providing cardiac ablation using a catheter, the ablation catheter 60 is advanced percutaneously through an introducing sheath (not shown) to a major artery in the area of the patient's groin and is then advanced through the artery to the heart 62. In a preferred embodiment the catheter includes a wire braid in its shaft to provide high torquability for permitting the physician to finely guide the catheter 60 to the site. The guiding catheter preferably includes a deflectable tip actuated from the proximal end of the catheter by a deflecting thumb actuator. Alternatively, the catheter may include a precurve at the distal end to permit the user, through rotation of the guiding catheter, to precisely control the location of the distal end of the catheter. Similarly, the ablation catheter 60 also includes at the distal end a precurved portion and is torquable to enable access to an extended region of the heart.

Such a catheter can be advantageously employed for cardiac mapping and ablation applications. Referring to FIGS. 9A–9B, a mapping/electro-coagulation catheter 60 is used to identify a potential problem area 64 of heart 62. Mapping/electro-coagulation catheter 60 includes a tissue penetrable probe 66 that is introduced to heart 62 through the vasculature or a guiding catheter. Probe 66 forms a first electrode of the electrode with a distal end 67 of the catheter 60 forming a second electrode which in cooperation with the probe electrode 66 provides bipolar electro-coagulation. Probe 66 is repeatedly projected into the heart and temporarily anchors the instrument at different locations within heart 62. At each location, the electrical condition is sensed between the electrodes until a problem area is encountered. Because the heart is beating it is often difficult to maintain the position of the catheter in position. For this reason, as shown in FIG. 9B, a sufficient sideways pressure (designated by arrow B) is applied to catheter 60 to provide resistance to removal of probe 66 from the tissue such that the catheter is secured or "anchored" in place. In this way, mapping of the electrical condition at each location can be made with greater confidence. In operation, a physician is able to repeatedly move catheter 60 to areas of heart 62 to make sensing measurements. FIG. 9A, in this case, represents a mapping made at an area of heart 62 without problem. As shown in FIG. 9B, upon arriving at problem area 64, a mapping indicates an electrical condition requiring ablation. The ablation can be performed using a defibrillator, a laser, or bipolar electrocoagulation as described above in conjunction with FIGS. 1–8.

Alternatively, cardiac mapping/ablation as described above in conjunction with FIGS. 9A–9B, may be accomplished using mono-polar (or unipolar) electrocoagulation techniques. An electrophysiology catheter is guided into a chamber of the heart to tissue requiring ablation. A fluoroscope is generally used to aid the physician in guiding the catheter to its appropriate position. Catheter includes at a distal end an extendable and retractable probe which in conjunction with a conductive patch placed on the outer body surface of the patient constitute first and second electrodes of the electrophysiology catheter. The patch is typically placed at the thigh area of the patient and is applied with a conductive gel to provide better electrical contact. Mapping of the electrical condition is performed at locations of the heart and upon an indication of a problem area the ablation procedure is performed.

Figure 10:
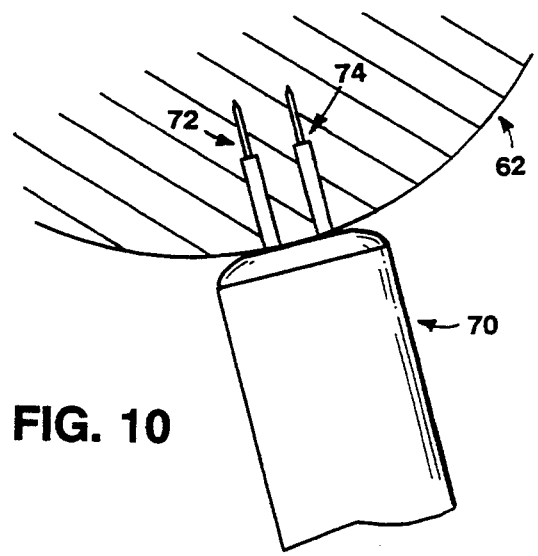
FIG. 10 is a diagrammatic view of an alternate embodiment of a catheter having multiple projectable probes.

As shown in FIG. 10, the sensing of the electrical condition at different locations of heart 62 may be accomplished using a catheter 70 having multiple projectable probes 72, 74 which are spaced from each other a predetermined distance. In this arrangement, electrical conditions sensed at each location will provide the physician to determine whether the electrical conduction in the heart is travelling smoothly between locations and if not determine the tissue area having the faulty conduction problem.

In a preferred embodiment, probe 64 includes a hollow center point needle similar to the one shown in FIG. 4 to permit the administration of a temporary anesthetic, such as Xylocaine. The anesthetic acts to temporarily numb the problem area so that a determination can be made as to whether the arrhythmia has been eliminated. If it has, the physician can proceed with the ablation procedure with greater confidence that the ablation will stop the arrhythmia.

Likewise, a sclerotic agent for enhancing electrocoagulation of the tissue or a heat-responsive drug may be introduced to the ablation site. It is known that heat improves the bonding of certain drugs to tissue surfaces. Such heat-responsive drugs are easily delivered to the subcutaneous tissue via a catheter having a probe 64 as shown in FIG. 4 and infused in place.

Thus it is seen the concept is one of providing the physician with multi modality capabilities to titrate the therapy to the desired result. The instrument provides an electric coagulation capability.

Other embodiments are within the scope of the claims.

What is claimed is:

1. An electro-coagulation constructed for passage into a living body to perform therapy on a selected region of body tissue, said catheter comprising
a flexible, pushable, elongated catheter body of braided construction having proximal and distal portions terminating respectively at proximal and distal ends defining a tube-receiving lumen having a length that extends from the proximal end of said catheter body to the distal end of said catheter body, said length being selected to perform therapy on selected regions of body tissue within the gastrointestinal tract or the esophagus of a patient while the proximal end of said catheter body remains outside the patient,
an RF electrocoagulation electrode coupled to the distal portion of said catheter body, said electrode being connected to a respective conductor extending within said catheter body,
a retractable, flexible hollow tube having a tissue-penetrable needle-form distal end and having a proximal end and extending within said tube-receiving lumen and along the entire length thereof, said flexible hollow tube having a fluid passage therethrough for introducing a fluid into the tissue in the selected region, said flexible hollow tube being selectively slidable within said tube-receiving lumen of said catheter body to cause said needle-form distal end of said flexible tube to be projectable from and retractable into the distal end of said catheter body by actuation force applied to the proximal end of said flexible hollow tube, and
means for remotely applying actuation force to the proximal end of said flexible hollow tube to cause said needle-form distal end of said flexible hollow tube to project from the distal end of said catheter body for penetration of tissue within the gastrointestinal tract or esophagus of the patient.

2. The catheter of claim 1 further comprising a second electrode coupled to the distal portion of said catheter body, said electrode and said second electrode being constructed and arranged to establish a bipolar RF electro-coagulation path through the selected region of body tissue.

3. The catheter of claim 2 wherein said electrode and said second electrode are arranged in a spaced-apart helical arrangement at the distal end of said catheter body.

4. The catheter of claim 1 wherein said electrode is a ring electrode.

5. The catheter of claim 1 wherein said applying means comprises a push-pull wire coupled to said needle for applying actuation force to said needle.

6. The catheter of claim 1 wherein the distal portion of said needle comprises electrically conducting material.

7. The catheter of claim 6 wherein said needle is connected to a respective conductor that extends within said catheter body for connection to an RF generator, said needle and said electrode being configured to establish therebetween a bipolar RF electro-coagulation path through the selected region of body tissue.

8. The catheter of claim 1 wherein the distal portion of said catheter body is dome-shaped and made from a refractory material, and wherein said electrode comprises a conductive metallic layer bonded to said refractory material.

9. The catheter of claim 1 further comprising a second retractable hollow needle, the distal portion of said second needle being selectively projectable from and retractable into the distal end of said catheter body by actuation force applied to the proximal portion of said second needle.

10. The catheter of claim 9 wherein said needle and said second needle have electrically conductive distal portions that are connected to respective conductors for connection to an RF generator, wherein said needle and said second needle, when projected into tissue, are capable of subsurface bipolar electrocoagulation therebetween.

11. The catheter of claim 1 further comprising
a selectively retractable sleeve disposed around at least a portion of said needle, and
means for selectively extending and retracting said sleeve independently of said needle so that, when said needle is extended, the exposed surface of the distal portion of said needle can be selectively varied by extension or retraction of said sleeve.

12. The catheter of claim 1 wherein said catheter body has at least one precurved portion capable of being elastically deformed to conform to an introducing channel through which it passes into the body, said catheter body being constructed to transmit torque from the proximal portion of said catheter body to the distal portion of said catheter body so that the orientation of said precurved portion can be adjusted by applying torque to the proximal portion of said catheter body.

13. The catheter of claim 1 further comprising proximal markings coupled to said force applying means that serve to identify the distance said needle is extended beyond the distal end of said catheter body, thereby enabling said needle to be controllably extended a desired length into tissue in the selected region.

14. The catheter of claim 1 further comprising a longitudinally extending irrigation passage through said catheter body for providing perfusion fluid to cleanse the selected region of body tissue.

15. A method of electro-coagulating a selected region of body tissue comprising the steps of
inserting into a living body a bipolar electro-coagulation catheter having proximal and distal portions respectively terminating at proximal and distal ends to the site of the selected region, said catheter comprising
a flexible, pushable, elongated catheter body of braided construction having proximal and distal portions terminating respectively at proximal and distal ends defining a tube-receiving lumen having a length that extends from the proximal end of said catheter body to the distal end of said catheter body, said length being selected to perform therapy on selected regions of body tissue within the gastrointestinal tract or the esophagus of a patient while the proximal end of said catheter body remains outside the patient,
first and second RF electrocoagulation electrodes coupled to the distal portion of said catheter body, said electrodes being connected to respective conductors extending within said catheter body, and
a retractable, flexible hollow tube having a tissue-penetrable needle-form distal end and having a proximal end and extending within said tube-receiving lumen and along the entire length thereof, said flexible hollow tube having a fluid passage therethrough for introducing a fluid into the tissue in the selected region, said flexible hollow tube being selectively slidable within said tube-receiving lumen of said catheter body to cause said needle-form distal end of said flexible tube to be projectable from and retractable into the distal end of said catheter body by actuation force applied to the proximal end of said flexible hollow tube, inserting said needle-form distal end of said flexible hollow tube into tissue in the selected region, contacting said first and second electrodes with the surface of tissue in the selected region, introducing a fluid into tissue in the selected region through said flexible hollow tube and needle-form distal end, and applying RF coagulation voltage between said first and second electrodes to effect bipolar electro-coagulation of the selected region of body tissue.

16. The method of claim 15 wherein said fluid comprises a heat-responsive drug.

17. The method of claim 15 wherein said fluid comprises a sclerotic agent.

18. The method of claim 15 wherein said fluid is a vaso-constrictive agent.

19. The method of claim 15 wherein the distal portion of said needle is electrically conductive and is electrically coupled to a respective conductor for connection to an RF generator, and wherein the step of applying comprises applying RF bipolar electro-coagulation voltage between the electrically conductive portion of said needle and at least one of said first and second electrodes.

* * * * *

UNITED STATES PATENT AND TRADEMARK OFFICE
CERTIFICATE OF CORRECTION

PATENT NO.    : 5,403,311

DATED         : April 4, 1995

INVENTOR(S)   : John E. Abele et al.

It is certified that error appears in the above-identified patent and that said Letters Patent is hereby corrected as shown below:

On the title page,
    In References Cited [56], U.S. PATENT DOCUMENTS, under 4,998,933 change "606/44" to --606/41--.

Col. 7, line 40; change "reduce" to read --to reduce the--.

Col. 11, line 1, before "constructed" insert --catheter--.

Signed and Sealed this

Twenty-eighth Day of May, 1996

Attest:

BRUCE LEHMAN

Attesting Officer        Commissioner of Patents and Trademarks